(12) United States Patent
Yayon et al.

(10) Patent No.: US 7,009,039 B2
(45) Date of Patent: Mar. 7, 2006

(54) PLASMA PROTEIN MATRICES AND METHODS FOR THEIR PREPARATION

(75) Inventors: Avner Yayon, Moshav Sitria (IL); Rachel Glicklis, Lehavim (IL)

(73) Assignee: ProChon Biotech Ltd., Rehovot (IL)

( * ) Notice: Subject to any disclaimer, the term of this patent is extended or adjusted under 35 U.S.C. 154(b) by 40 days.

(21) Appl. No.: 10/761,615

(22) Filed: Jan. 20, 2004

(65) Prior Publication Data

US 2004/0209359 A1    Oct. 21, 2004

Related U.S. Application Data

(63) Continuation of application No. PCT/IL02/00589, filed on Jul. 18, 2002.

(30) Foreign Application Priority Data

Jul. 19, 2001    (IL) ..................... 144446

(51) Int. Cl.
*A61K 35/14* (2006.01)
*A61K 38/00* (2006.01)
(52) U.S. Cl. ............... 530/381; 424/93.7; 424/422; 602/48; 514/12
(58) Field of Classification Search .......... 424/93.7, 424/400, 422; 602/48; 514/12; 530/381
See application file for complete search history.

(56) References Cited

U.S. PATENT DOCUMENTS

| | | | |
|---|---|---|---|
| 4,442,655 A | 4/1984 | Stroetmann | 53/428 |
| 4,642,120 A | 2/1987 | Nevo et al. | 623/16 |
| 4,971,954 A | 11/1990 | Brodsky et al. | 514/21 |
| 5,260,420 A | 11/1993 | Burnouf-Radosevich et al. | 530/382 |
| 5,411,885 A | 5/1995 | Marx | 435/240 |
| 5,443,950 A | 8/1995 | Naughton et al. | 435/1 |
| 5,631,011 A * | 5/1997 | Wadstrom | 424/400 |
| 5,700,476 A | 12/1997 | Rosenthal et al. | 424/426 |
| 5,736,372 A | 4/1998 | Vacanti et al. | 435/180 |
| 5,842,477 A | 12/1998 | Naughton et al. | 128/898 |
| 5,948,429 A | 9/1999 | Bell et al. | 424/426 |
| 5,955,438 A | 9/1999 | Pitaru et al. | 514/21 |
| 5,974,663 A | 11/1999 | Ikeda et al. | 29/888.09 |
| 6,090,996 A * | 7/2000 | Li | 623/23.64 |
| 6,274,090 B1 | 8/2001 | Coelho et al. | 422/101 |
| 6,274,663 B1 | 8/2001 | Hosokawa et al. | 524/442 |
| 6,293,970 B1 * | 9/2001 | Wolfinbarger et al. | 623/23.61 |
| 6,310,267 B1 | 10/2001 | Rapp | 602/41 |
| 6,398,816 B1 | 6/2002 | Breitbart et al. | 623/23.72 |
| 6,548,729 B1 * | 4/2003 | Seelich et al. | 602/48 |
| 6,599,515 B1 | 7/2003 | Delmotte | 424/422 |

FOREIGN PATENT DOCUMENTS

| | | | |
|---|---|---|---|
| GB | 2102811 | * | 2/1983 |
| WO | WO 98/43686 A1 | | 10/1998 |
| WO | WO 99/15209 | | 4/1999 |
| WO | WO 02/18546 A2 | | 3/2002 |

OTHER PUBLICATIONS

"Young's Modulus." Entry on http://en.wikipedia.org, accessed Oct. 27, 2005. 3 pages.*
Marion M. Bradford, "A Rapid and Sensitive Method for the Quantitation of Microgram Quantities of Protein Utilizing the Principle of Protein-Dye Binding" Analytical Biochemistry, vol. 72, pp. 248-254 (1976).
E. B. Hunziker, "Articular cartilage repair: basic science and clinical progress. A review of the current status and prospects", OsteoArthritis Research Society International,. Published by Elsevier Science Ltd. Osteoarthritis and Cartilage, vol. 10, pp. 432-463 (2001).
Sims, C. Derek M.D. et al. "Tissue Engineered Neocartilage Using Plasma Derived Polymer Substrates and Chondrocytes", Boston and Cambridge, Mass., vol. 101(6), pp 1580-1585, (1998).
A. Haisch et al., "Preparation of a pure autologous biodegradable fibrin matrix for tissue engineering", Cellular Engineering, Medical & Biological Engineerin & Computing, vol. 38, pp. 686-689 (2000).

* cited by examiner

*Primary Examiner*—Sandra E. Saucier
*Assistant Examiner*—Lora E Barnhart
(74) *Attorney, Agent, or Firm*—Winston & Strawn LLP

(57) ABSTRACT

A freeze dried biocompatible matrix comprising plasma proteins, useful as implants for tissue engineering as well as in biotechnology, and methods of producing the matrix are provided. Mechanical and physical parameters can be controlled by use of auxiliary components or additives which may be removed after the matrix is formed in order to improve the biological properties of the matrix. The matrices according to the present invention may be used clinically per se, or as a cell-bearing implant.

53 Claims, 7 Drawing Sheets

FIGURE 4
FIG. 4B
FIG. 4D
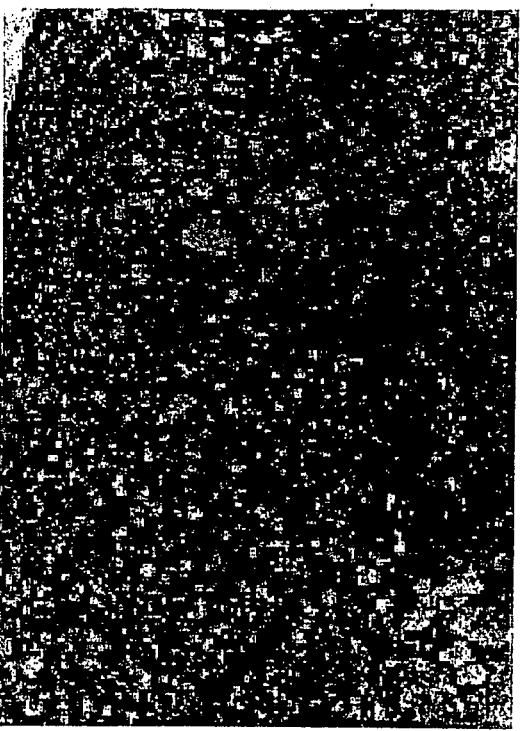
FIG. 4A
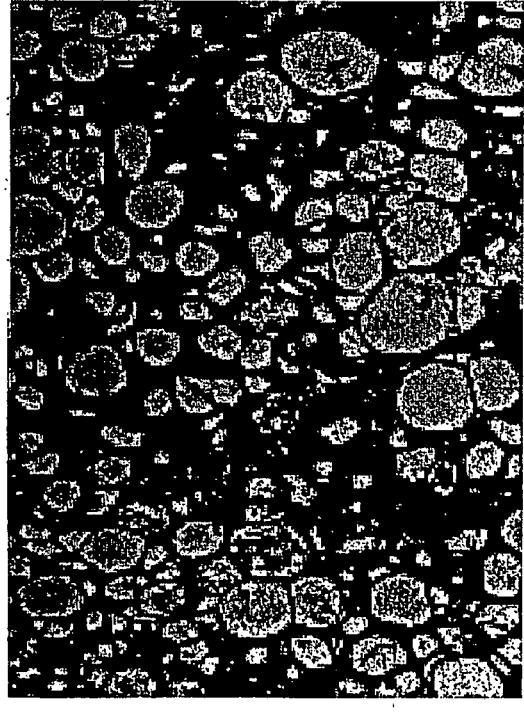
FIG. 4C
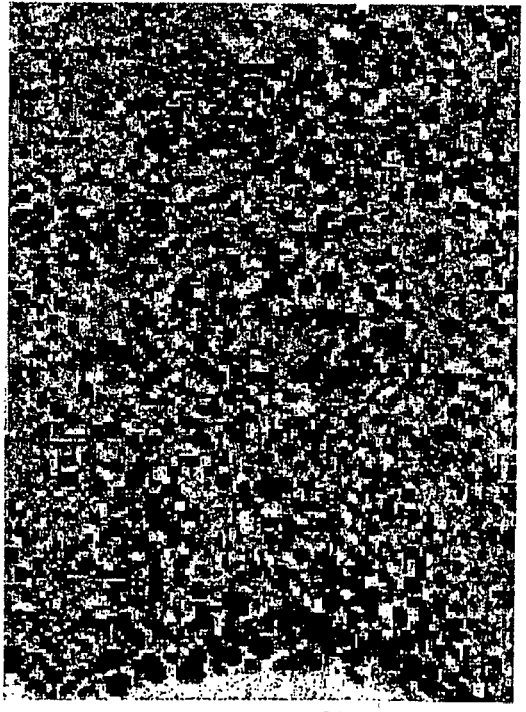

A Goat 2

D Goat 183

B Goat 143

E Goat 930

C Goat 943

F Goat 945

PLASMA PROTEIN MATRICES AND METHODS FOR THEIR PREPARATION

This is a continuation of Application No. PCT/IL02/00589, filed Jul. 18, 2002.

FIELD OF THE INVENTION

The present invention concerns biomatrices comprising freeze-dried plasma proteins useful for clinical applications including as implants for tissue engineering as well as in biotechnology. The matrices according to the present invention may be used clinically, per se or as cell-bearing implants.

BACKGROUND OF THE INVENTION

Tissue engineering may be defined as the art of reconstructing mammalian tissues, both structurally and functionally (Hunziker, 2002). In vitro tissue engineering generally includes the delivery of a polymeric scaffold that serves as an architectural support onto which cells may attach, proliferate, and synthesize new tissue to repair a wound or defect An example of a tissue that is prone to damage by disease and trauma is the articular cartilage, one of several types of cartilage in the body, found at the articular surfaces of bones. Damage to cartilage may result from an inflammatory disease such as rheumatoid arthritis, from a degenerative process such as osteoarthritis or from trauma such as intraarticular fracture or following ligament injuries. Cartilage lesions are often associated with pain and reduced function and generally do not heal without medical intervention.

Current therapeutic strategies for repairing damaged cartilage include procedures which induce a spontaneous repair response and those which reconstruct the tissue in a structural and functional manner. The former, including surgical techniques such as abrasion artheroplasty, microfracture or subchondral micro-drilling, expose the subchondral region of bone thereby allowing the formation of a blood clot and infiltration of pluripotent stem cells to initiate the healing response. Often the induced tissue is not durable and the clinical improvements are short lived.

An alternative is transplantation of chondral or osteochondral tissue from either autologous or allogeneic sources. The rationale behind transplantation lies in the notion that the proliferative and tissue-differentiation activities of these cells would result in the formation of neocartilage. In fact, this technique shows high variability and limited clinical success.

Matrices useful for tissue regeneration and/or as biocompatible surfaces useful for tissue culture are well known in the art. These matrices may therefore be considered as substrates for cell growth either in vitro or in vivo. Suitable matrices for tissue growth and/or regeneration include both biodegradable and biostable entities. Among the many candidates that may serve as useful matrices claimed to support tissue growth or regeneration, are included gels, foams, sheets, and numerous porous particulate structures of different forms and shapes.

Porous materials formed from synthetic and/or naturally occurring biodegradable materials have been used in the past as wound dressings or implants. The porous material provides structural support and a framework for tissue in-growth while healing progresses. Preferably, the porous material is gradually absorbed as the tissue around the wound regenerates. Typical bioabsorbable materials for use in the fabrication of porous wound dressings or implants include both synthetic polymers and biopolymers such as structural proteins and polysaccharides. The biopolymers may be either selected or manipulated in ways that affect their physico-chemical properties. For example biopolymers may be cross linked either enzymatically, chemically or by other means, thereby providing greater or lesser degrees of flexibility or susceptibility to degradation.

Among the manifold natural polymers which have been disclosed to be useful for tissue engineering or culture, one can enumerate various constituents of the extracellular matrix including fibronectin, various types of collagen, and laminin, as well as keratin, fibrin and fibrinogen, hyaluronic acid, heparan sulfate, chondroitin sulfate and others.

Fibrin is a major plasma protein which participates in the blood coagulation process. The coagulation of blood is a complex process including the sequential interaction of a number of plasma proteins, in particular of fibrinogen (factor I); factor II, factor V, factor VII, factor VIII, factor IX, factor X, factor XI, factor XII and factor XIII.

Other plasma proteins such as Von Willebrand factor (vWF), albumin, immunoglobulin, coagulation factors, and complement components may also play a part in the formation of protein networks or clots in the blood.

Fibrin is known in the art as a tissue adhesive medical device and can be used in wound healing and tissue repair. Lyophilized plasma-derived protein concentrate (containing Factor XIII, fibronectin, and fibrinogen), in the presence of thrombin and calcium forms an injectable biological glue. U.S. Pat. No. 5,411,885 discloses a method of embedding and culturing tissue employing fibrin glue. U.S. Pat. No. 4,642,120 discloses the use of fibrinogen glue in combination with autologous mesenchymal or chondrocytic cells to promote repair of cartilage and bone defects. U.S. Pat. No. 5,260,420, discloses a method for preparation and usage of biological glue comprising fibrin for injection at the site of injury. U.S. Pat. No. 6,074,663 discloses a cross-linked fibrin sheet-like material for the prevention of adhesion formation.

U.S. Pat. No. 6,310,267 discloses a specific process for preparing a biodegradable flexible fibrin web for wound healing. The process necessitates dialyzing a fibrinogen solution with a solution containing chelators and forming the flexible web by the addition of a thrombin solution, freeze drying and lyophilizing the web.

U.S. Pat. No. 5,972,385 discloses a cross-Linked collagen-polysaccharide matrix that is administered alone or in combination with other therapeutics, such as growth factors, for tissue repair. The invention also discloses the cross-linked collagen-polysaccharide matrix in combination with fibrin. The matrix preparation steps include freezing and lyophilization as well as adding fibrinogen and thrombin to form fibrin in said matrix.

A freeze-dried fibrin web for wound healing has been disclosed in U.S. Pat. No. 6,310,267. The preparation of the web, as disclosed, requires a single- or multistage dialysis of the fibrinogen solution. According to that disclosure, the single-stage or multistage dialysis of the fibrinogen solution crucially changes its composition and the concentration of salts and amino acids customarily contained in it are considerably reduced. The dialysis is carried out in an aqueous solution of a physiologically compatible inorganic salt such as NaCl and an organic complexing agent such as alkali metal salts of EDTA, of oxalic acid or of citric acid.

A fibrin sponge containing a blood clotting activator for hemostasis, tissue adhesion, wound healing and cell culture support is disclosed in WO 99/15209.

According to that disclosure, the restoration of moisture or water content following lyophilization is crucial for obtaining a soft, adaptable, highly, absorbent sponge.

U.S. Pat. Nos. 5,955,438 and 4,971,954 disclose collagen-based matrices cross-linked by sugars, useful for tissue regeneration. U.S. Pat. No.5,700,476 provides a bioabsorbable implant material containing pharmacologically active agents, suitable for use in wound repair. The method describes the mixture of two biopolymer components, freeze dried to form a heteromorphic sponge, that allows a phased release of a pharmacologically active agent.

U.S. Pat. No. 5,736,372 discloses a biodegradable synthetic polymeric fibrous matrix containing chondrocytes for in vivo production of a functional cartilaginous structure to be used in joint lining.

U.S. Pat. No. 5,948,429 discloses a method of preparing a biopolymer foam comprising forming a biopolymer solution, cross-linking said solution with ultraviolet radiation and subsequently freeze-drying to form a lattice.

U.S. Pat. No. 5,443,950 relates to a method for implantation of a variety of cell types growing on a three dimensional cell matrix which has been inoculated with stromal cells to form a three dimensional stromal matrix. Further disclosed in U.S. Pat. No. 5,842,477 is a method of in vivo cartilage repair by implanting a biocompatible three dimensional scaffold in combination with periosteal/perichondrial tissue and stromal cells, with or without bioactive agents, for the production of new cartilage at the site of implantation. The scaffold used is selected from a group consisting of biodegradable or non-biodegradable materials.

There is an unmet need for a treatment for tissue defects, including but not limited to those found in diseased or injured cartilage and bone. Nowhere in the background art is it taught or suggested that mechanical and physical parameters of freeze-dried matrices composed of plasma proteins can be controlled by use of auxiliary components or additives, which may be removed after the matrix is formed, in order to improve the biological properties of the matrix. The matrices of the invention are useful for cellular growth, as an implant per se and/or as a cell-bearing implant suitable for transplantation.

SUMMARY OF THE INVENTION

It is an object of the present invention to provide a porous matrix that is useful as a support for growth of cells, both in vitro and in vivo. It is another object of the present invention to provide a matrix that is biodegradable and non-immunogenic. It is yet another object of the present invention to provide a porous matrix that is useful as an implant per se, or as a cell-bearing implant for repairing tissue damaged by disease or trauma. It is a further object of the present invention to provide a method of promoting growth and repair of cartilage in vivo. It is yet a ether object of the present invention to provide methods for preparing said matrix.

These and other objects are met by the invention disclosed herein.

Though numerous biomatrices comprising various plasma or tissue proteins are known in the background art, none has proven entirely satisfactory in meeting the criteria required for successful tissue engineering. The porous matrix disclosed herein, also referred to as a sponge, has attributes that make it particularly advantageous for supporting and promoting cell growth both in vivo and in vitro. Among the advantageous properties of the matrices of the invention:

1. The matrices can be formed successfully with partially purified proteins, such as crude fractions of plasma proteins.
2. The plasma proteins can be retrieved from autologous material thereby obviating the need for pooled blood sources with the attendant health risks.
3. The matrices have superior mechanical properties, controlled by varying auxiliary components used in the composition. Desirable properties include tensile strength, elasticity, compressibility, resistance to shear, moldability.
4. The matrices have superior physical properties, controlled by varying auxiliary components used in the composition. Desirable properties include texture, pore size and uniformity of pores, charge and charge distribution, hydrophilicity, adhesion, wettability.
5. The matrices have superior biological properties, controlled by varying auxiliary components used in the composition. Desirable properties include biodegradability, lack of immunogenicity, the capacity to maintain and promote cell growth, proliferation, differentiation and migration.

It is now disclosed for the first time that the attributes and desirable properties of the matrices can be controlled by the use of auxiliary components, some of which might be considered detrimental to the subsequent support of cell growth and proliferation. It is therefore explicitly intended to be understood that these components be utilized in the processes of generating and formation of the freeze dried matrices, and then removed as necessary. The lyophilized matrices may be rehydrated and washed to remove any such additives that are deleterious to cell growth, thereby providing optimized plasma protein matrices with the desired mechanical and biological properties for the intended use, essentially free of the components detrimental to cell growth. The washed matrices can be used directly or re-lyophilized prior to use.

The essential constituents of the matrices of the invention are fibrin, obtained by the interaction of fibrinogen and thrombin, in the presence of calcium ions and Factor XIII; anti-fibrinolytic agents, as are well known in the art, selected from serine protein inhibitors, especially plasmin inhibitors, particularly tranexamic acid. Other antifibrinolytics may be used, alone or in combination, including aprotinin, $\alpha$-2-macroglobulin, $\alpha$-2-plasmin inhibitor, plasminogen activator inhibitor and other natural or synthetic agents. These essential components, with or without any optional additives, are freeze-dried to obtain a resilient sponge-like matrix, substantially in the absence of organic chelating agents, with no minimal requirement of residual water content The auxiliary components include various polymers that impart the desired properties as detailed above. The preferred polymers may be selected from: polysaccharides, currently more preferred hyaluronic acid; anionic polysaccharides, currently more preferred being sulfated polysaccharides, currently most preferred being dextran sulfate; glycosaminoglycans, or other polymers such as polyethylene glycols or combinations thereof. Furthermore, glycerol may be added in conjunction with one or more of the above components.

The present invention provides an inexpensive, biodegradable, non-immunogenic three-dimensional matrix of plasma-derived proteins. In currently preferred embodiments of the present invention, the matrix comprises plasma proteins from allogeneic plasma, more preferably from autologous plasma. According to one embodiment of the present invention, at least one of the plasma proteins used for preparing the matrix is derived from autologous plasma. According to another embodiment of the invention all of plasma proteins are derived from autologous plasma. However, plasma proteins from any immunologically or otherwise suitable source may be used, as well as engineered proteins or peptides having the capability to form, upon reaction with thrombin and factor XIII, a plasma protein clot. Thus, in one embodiment of the invention, the plasma proteins utilized in the present invention include at least fibrinogen and factor XIII. These components may be purified from a plasma source or may be used from a commercially available source, including native or recombinant proteins.

In one embodiment of the present invention the plasma protein matrix is a sponge having tensile strength of at least 0.2 kPa and 2 mm deformation, measured as described herein below. The sponge matrix of the invention may have irregular pores or substantially regular pores. In the specification and the claims the term substantially regular pores means that the majority of the pores or more preferably substantially all the pores are in the same size range. More preferred matrices according to the invention have pores of a diameter in the range of 50–300 microns. Currently most preferred embodiments according to the present invention are plasma protein sponge matrices with pore sizes in the range of 100–200 $\mu$m.

The plasma protein matrix having the above specified structural and mechanical properties may be obtained by any appropriate method, the currently preferred method being freeze drying a plasma protein clot In one embodiment of the invention the plasma matrix is prepared by mixing plasma proteins with thrombin in the presence of calcium chloride under conditions suitable for achieving clotting; casting or molding the mixture of plasma proteins and thrombin in a solid support prior to achieving clotting; freezing the clotted mixture; and lyophilizing the clotted mixture. Alternatively, the thrombin solution may be poured into a mold, the fibrinogen solution added and mixed to blend; the clotted mixture frozen and lyophilized.

The method for preparing a matrix of plasma proteins useful as a scaffold for growing cells, as a scaffold for implantation in vivo or in situ comprises the following steps:

mixing plasma proteins with thrombin in the presence of calcium ions and at least one anti-fibrinolytic agent under conditions suitable for achieving clotting, in the substantial absence of organic chelating agents, and optionally adding at least one auxiliary component;

casting the mixture of plasma proteins and thrombin in a solid support prior to achieving clotting;

freezing the clotted mixture; and lyophilizing the clotted mixture, to obtain a sponge having no more than 3% residual moisture.

In one particular exemplary embodiment plasma proteins at a concentration of 30–50 mg/ml are mixed with at least 0.5 units, preferably 1.5 units of thrombin per mg total plasma protein, and then the mixture is frozen at −70° C. for approximately 16 hours and lyophilized for at least 16 hours, preferably 24 hours.

In its final form prior to use with cells the sponge is substantially dry and contains less than 10% residual moisture, more preferably less than 5% residual moisture and most preferably less than 3% residual moisture.

In another preferred embodiment the sponge of the present invention contains auxiliary components which may modify certain properties of the sponge including physical, mechanical and/or biological properties. The addition of the auxiliary components, imparts superior characteristics to the sponge. The auxiliary components are added to the plasma proteins prior to the formation of a clot. A currently preferred embodiment in accordance with the present invention is a sponge comprising dextran sulfate. A currently more preferred embodiment in accordance with the present invention is a sponge comprising hyaluronic acid. A currently most preferred embodiment in accordance with the present invention is a sponge comprising hyaluronic acid and glycerol.

In yet another preferred embodiment, the additives which impart beneficial properties to the sponge are removed and the sponge lyophilized to remove all moisture. Once the sponge is cast and lyophilized, the additives are no longer required and may be removed from the sponge. A currently preferred embodiment provides a sponge prepared containing at least one as described above, wherein the sponge is washed following the freezing-lyophilization step and the sponge re-lyophilized to remove residual moisture.

The present invention also provides for the introduction of additional synthetic polymers into the sponge, during the preparation procedure. These polymers may change the physical, mechanical and or biological properties of the sponge. The polymers may be non-biodegradable or biodegradable. Examples non-degradable materials include polytetrafluoroethylene, perfluorinated polymers such as fluorinated ethylene propylene, polypropylene, polyethylene, polyethylene terapthalate, silicone, silicone rubber, polysufone, polyurethane, non-degradable polycarboxylate, non-degradable polycarbonate, non-degradable polyester, polyacrylic, polyhydroxymethacrylate, polymethylmethacrylate, polyamide such as polyesteramide, and copolymers, block copolymers and blends of the above materials.

Examples of degradable materials include hydrolyzable polyesters such as polylactic acid and polyglycolic acid, polyorthoesters, degradable polycarboxylates, degradable polycarbonates, degradable polycaprolactones, polyanhydride, and copolymers, block copolymers and blends of the above materials. Other components include surfactants including lecithin.

The plasma protein matrix of the invention is useful, inter alia, as an unexpectedly advantageous support for cellular growth. The matrix of the present invention is a biocompatible surface useful for tissue culture, such as for growing mesenchymal cells, chondrocytes, osteocytes and osteoblasts, epithelial cells, neuronal cells, hepatic, renal, pancreatic and any other cell types which it is desired to culture within a three dimensional support.

Further provided by the present invention is a cell bearing implant for transplanting cells in vivo. According to one currently preferred embodiment of the present invention the matrix is a sponge comprising plasma proteins able to support the proliferation of a variety of cell types. Preferably, the sponge is inoculated with cells and the cells allowed to proliferate in vitro prior to in vivo implantation. Alternatively, the sponge is allowed to absorb cells that have been cultured or harvested and the sponge comprising the cells is implanted in vivo.

Furthermore, there is also included the introduction into the sponge of an auxiliary component which is a bioactive agent selected from growth factors, cytokines, enzymes, anti-microbials, anti-inflammatory agents.

The bioactive agents, for example, growth factors, aneiogenic factors, and the like, are advantageous to encourage a more rapid growth of the cells within the implant, or a more rapid vascularization of the implant.

The implant consists of a plasma protein scaffold bearing cells at a density that is at least $10^4$ (ten thousand) cells per $cm^3$, preferably $10^5$ cells per $cm^3$, more preferably $10^6$ cells per $cm^3$. In a non-limiting example, an implant for transplanting chondrocytes to a site of cartilage damage consists of a 300 $\mu$l plasma protein scaffold having an approximate volume of 0.2 $cm^3$, having $10^4$ chondrocytes seeded therein prior to a 2–3 day incubation period. Preferably, a plasma protein scaffold for transplanting chondrocytes comprising autologous plasma proteins and autologous chondrocytes is used as an implant for transplantation. In a particular embodiment of the invention a plasma protein scaffold for transplanting chondrocytes comprises a fibrin sponge having a substantially regular pore size of 50–300 µm and a 0.2 kPa. The plasma protein matrix of the invention may be cut into sections of desired size and shape to fit the affected area prior to seeding with cells or prior to implantation.

The plasma protein scaffold may also be used as an implant per se, for providing mechanical support to a defective or injured site in situ and/or for providing a matrix within which cells from the defective or injured site proliferate and differentiate. For example, for cartilage repair the plasma protein matrix may be used in conjunction with other therapeutic procedures including chondral shaving, laser or abrasion chondroplasty, drilling or microfracture techniques.

The plasma protein matrix of the invention, being an effective scaffold supporting cell growth, may further be utilized in vivo in reconstructive surgery, for example as a matrix for regenerating cells and tissue including neuronal cells, cardiovascular tissue, urothelial cells and breast tissue. Some typical orthopedic applications include joint resurfacing, meniscus repair, craniofacial reconstruction or repair of an invertebral disc. Furthermore, the plasma protein matrix may be used as a coating on synthetic or other implants such as pins and plates, for example, in hip replacement procedures. Thus, the present invention further provides implants or medical devices coated with the comprising the plasma protein matrix of the invention.

BRIEF DESCRIPTION OF THE FIGURES

The present invention will be understood and appreciated more fully from the following detailed description taken in conjunction with the figures in which:

FIGS. 4A–D show chondrocytes grown on the plasma protein matrix in accordance with an embodiment of the invention;

DETAILED DESCRIPTION OF THE INVENTION

Figure 1:
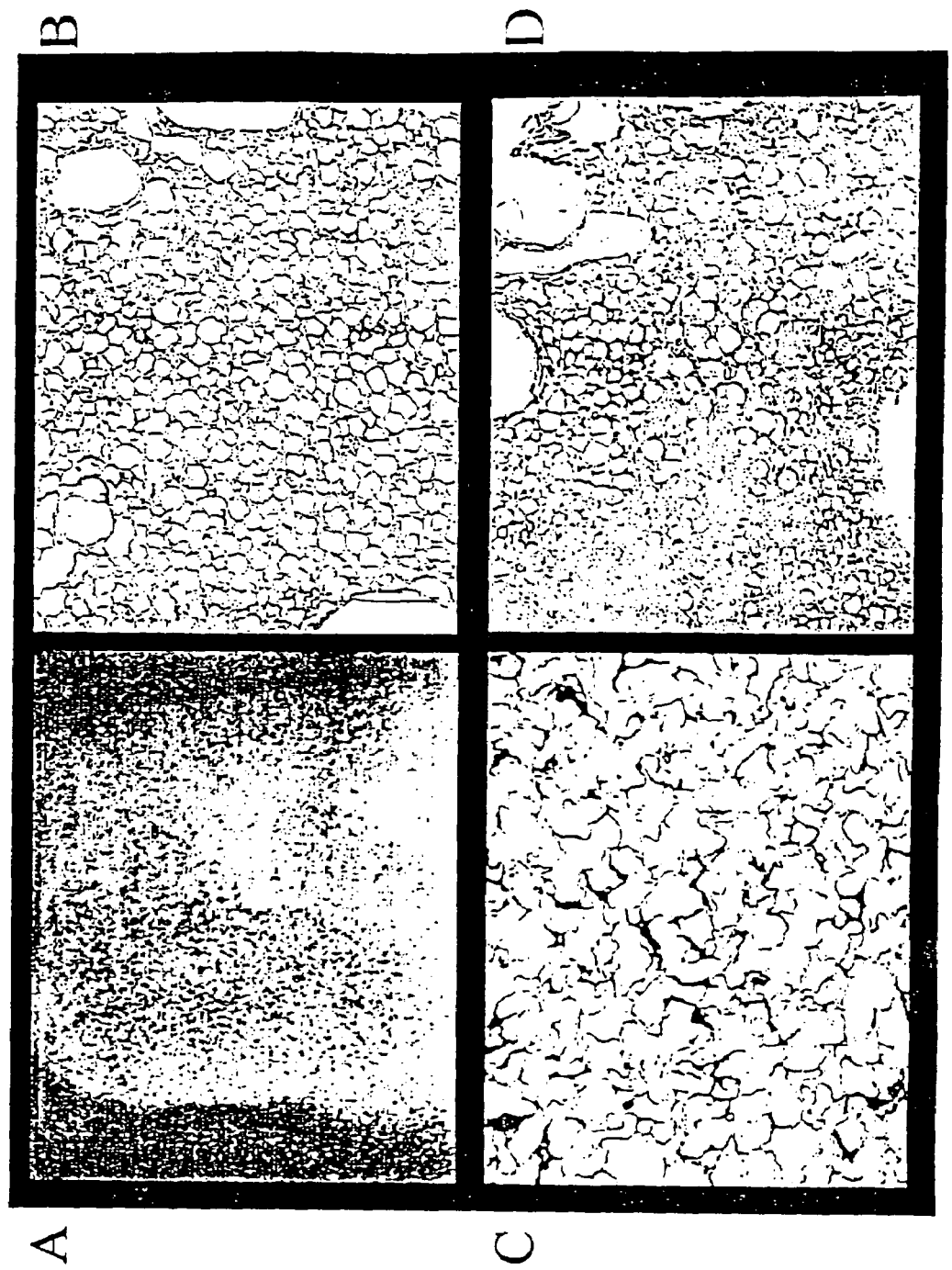
FIGS. 1A–D show a fibrin sponge prepared according to an embodiment of the invention prior to being freeze dried, after freeze drying, prepared using low fibrinogen concentration or high fibrinogen concentration and compared to a commercially collagen sponge.

The present invention relates to a freeze-dried, biocompatible, biodegradable matrix of plasma-derived proteins. The matrix according to an embodiment of the invention is useful in methods for regenerating and/or repairing various tissues in vivo, for example in tissue engineering methods, and for grouping cells in vitro.

The matrix of the present invention can be utilized in reconstructive surgery methods for regenerating and/or repairing tissue that have been damaged for example by trauma, surgical procedures or disease. The present invention provides a matrix for use as an implantable scaffold per se for tissue regeneration. According to a currently preferred embodiment of the invention, the matrix serves both as a physical support and an adhesive substrate for isolated cells during in vitro culture and subsequent implantation. As the transplanted cell populations grow and the cells function normally, they begin to secrete their own extracellular matrix (ECM) support. The scaffold polymer is selected to degrade as the need for an artificial support diminishes.

Scaffold applications include the regeneration of tissues such as neuronal musculoskeletal, cartilaginous, tendenous, hepatic, pancreatic, renal, ocular, arteriovenous, urinary or any other tissue forming solid or hollow organs. In a certain embodiment of the present invention stem cells derived from any tissue or induced to differentiate into a specific tissue type may be utilized. Preferably the cells are derived from autologous tissue. For example, for culturing cartilage, chondrocytes or mesenchymal stem cells may be seeded on the matrix. In specific embodiments of the invention, chondrocytes or chondrocyte progenitor cells can be seeded on the matrix prior to implantation or at the site of implantation in vivo. Additionally, the cell of interest may be engineered to express a gene product which would exert a therapeutic effect, for example anti-inflammatory peptides or proteins, growth factors having angiogenic, chemotactic, osteogenic or proliferative effects. A non-limitative example of genetically engineering cells to enhance healing is disclosed in U.S. Pat. No. 6,398,816.

In yet further embodiments of the invention, the matrix can be utilized as a coating of synthetic or other implants or medical devices. The matrix of the invention may be applied to implants such as pins or plates by coating or adhering methods known to persons skilled in the art. The matrix coating, which is capable of supporting and facilitating cellular growth, can thus be useful in providing a favorable environment for the implant.

For convenience and clarity certain terms employed in the specification, examples and claims are described herein.

"Plasma" as used herein refers to the fluid, non-cellular portion of the blood of humans or animals as found prior to coagulation.

"Plasma protein" as used herein refers to the soluble proteins found in the plasma of normal humans or animals. These include but are not limited to coagulation proteins, albumin, lipoproteins and complement proteins.

A "matrix" as used herein, refers to a porous structure, solid or semi-solid biodegradable substance having pores or spaces sufficiently large to allow cells to populate, or invade, the matrix. Matrix-forming materials may require addition of a polymerizing agent to form a matrix, such as addition of thrombin to a solution containing fibrinogen to form a fibrin matrix. The plasma protein matrix of the present invention may be denoted herein as a scaffold or as a sponge, for the culturing of cells, as a tissue replacement implant or as a cell-bearing tissue replacement implant.

The term "biocompatible" as used herein refers to materials which have low toxicity, acceptable foreign body reactions in the living body, and affinity with living tissues.

The term "cell-bearing" as used herein refers to the capacity of the matrix to allow cells to be maintained within the structure being referred to. Preferably, the cells are able to proliferate and invade the pores of the matrix.

This term "implantation" refers to the insertion of a sponge of the invention into a patient, whereby the implant serves to replace, fully or partially, tissue that has been damaged or removed. Another aspect of implantation is also taken to mean the use of the sponge as a vehicle to transport therapeutic drugs to a certain site in a patient. In this aspect there is also included the introduction into the sponge of an auxiliary component which is a bioactive agent selected from growth factors, cytokines, enzymes, anti-microbials, anti-inflammatory agents.

The bioactive agents, for example, growth factors, angiogenic factors, and the like, are advantageous to encourage a more rapid growth of the cells within the implant, or a more rapid vascularization of the implant Such factors may be too small to be effectively retained within the sponge and hence are introduced in the form of slow-release or controlled-release microcapsules into the sponge to provide for their effectivity.

The "pore size" of a pore within a plasma protein sponge is determined by using the equation: $P=(L \times H)^{1/2}$ wherein, L and H are the average length and height of the pores, respectively, as determined by microscopic analysis of the various sponges. The "pore wall thickness" is a parameter that characterizes the distance between the pores within a sponge and is indicative of the microstructure of the sponges. It is determined by measurement at the microscopic level.

"Surfactant" refers to a substance that alters energy relationship at interfaces, such as, for example, synthetic organic compounds displaying surface activity, including, inter alia, wetting agents, detergents, penetrants, spreaders, dispersing agents, and foaming agents. Preferable examples of surfactants useful in the present invention are hydrophobic compounds, and include phospholipids, oils, and fluorosurfactants.

The term "dry" and variations thereof, refer to a physical state that is dehydrated or anhydrous, i.e., substantially lacking liquid. The plasma protein matrices of the invention preferably having less than 10% residual moisture, more preferably having less that 5% residual moisture, most preferably having less that 5% residual moisture.

The terms "lyophilize" or "freeze drying" refer to the preparation of a composition in dry form by rapid freezing and dehydration in the frozen state (sometimes referred to as sublimation). This process may take place under vacuum at reduced air pressure resulting in drying at a lower temperature than required at full pressure.

An "anionic polysaccharide" as used herein, is a polysaccharide, including non-modified as well as chemical derivatives thereof, that contains one negatively charged group (e.g., carboxyl groups at pH values above about 4.0) and includes salts thereof, such as sodium or potassium salts, alkaline earth metal salts such as calcium or magnesium salts. Examples of anionic polysaccharides include pectin, alginate, galactans, galactomannans, glucomannans and polyuronic acids.

Examples of sulfated polysaccharides include heparin, chondroitin sulfate, dextran sulfate, dermatan sulfate, heparan sulfate, keratan sulfate, hexuronyl hexosaminoglycan sulfate, inositol hexasulfate, sucrose octasulfate. Derivatives and mimetics of the above are intended to be included in the invention.

The term "cartilage" as used herein, refers to a specialized type of connective tissue that contains chondrocytes embedded in an extracellular matrix. The biochemical composition of cartilage differs according to type but in general comprises collagen, predominantly type II collagen along with other minor types, e.g., types IX and XI, proteoglycans, other proteins, and water. Several types of cartilage are recognized in the art, including, for example, hyaline cartilage, articular cartilage, costal cartilage, fibrous cartilage, meniscal cartilage, elastic cartilage, auricular cartilage, and yellow cartilage. The production of any type of cartilage is intended to fall within the scope of the invention.

The term "chondrocytes" as used herein, refers to cells which are capable of producing components of cartilage tissue.

A "substantial absence of organic chelating agents" refers to a concentration less than 1 mm, for example less than 1 mm EDTA.

In one currently preferred embodiment of the present invention a plasma protein matrix is provided. The matrix of this type may be produced according to the invention by exposing a plasma protein solution containing an anti-fibrinolytic agent to a thrombin solution, subjecting said mixture to freezing and lyophilization to produce a sponge-like matrix.

U.S. Pat. No. 6,310,267 discloses a specific process for preparing a biodegradable flexible fibrin web for wound healing. The process necessitates dialyzing a fibrinogen solution with a solution containing chelators and forming the flexible web by the addition of a thrombin solution, freeze-drying and lyophilizing the web.

In contrast to fibrin webs of the background art the present inventors have unexpectedly discovered that a biocompatible, three-dimensional (3D) sponge-like matrix may be prepared from a crude plasma protein solution. A plasma protein scaffold or sponge with advantageous properties including adherence to tissue, pore size and biocompatibility is obtained following dialyzing out any organic complexing agents. According to one currently preferred embodiment of the present invention the plasma protein solution derives from allogeneic plasma. According to one currently more preferred embodiment of the present invention, at least one of the components, preferably the plasma proteins, used for preparing the matrix is derived from autologous plasma. According to another embodiment of the present invention, all of the components used in preparing the matrix are autologous. The plasma proteins may be isolated by a variety of methods, as known in the art and exemplified herein below, resulting in a plasma protein matrix having substantially similar properties, as measured by pore size, elasticity, compression and cell bearing capabilities. A stable thrombin component may be isolated from autologous plasma, according to methods known in the art for example those disclosed in U.S. Pat. No. 6,274,090 and Haisch et al (Med Biol Eng Comput 38:686–9, 2000).

The resulting plasma protein matrix exhibits advantageous properties including biocompatibility, pore size compatible with cell invasion and proliferation and ability to be molded or cast into definite shapes.

In a currently preferred embodiment of the present invention, blood is drawn from a patient in need of tissue repair or regeneration, plasma proteins are isolated from the autologous plasma and a matrix prepared thereof. The matrix of the present invention may serve as a support or scaffold per se or as a cell-bearing scaffold for in vivo implantation.

While not wishing to be bound by any particular theory the substantial absence of organic complexing agents may provide the matrix of the present invention with properties beneficial to the proliferation and metabolism of certain cell types. As shown in the examples herein, the matrix of the present invention supports the proliferation of cartilage cells in both in vivo and in vitro systems.

The presence of certain organic complexing agents in a range of 1 to 20 mM, necessary for the production of a flexible fibrin web disclosed in U.S. Pat. No. 6,310,267 for wound healing, may in itself have a detrimental effect on the proliferation of certain cell types. The use of a fibrin web for cell growth and proliferation, in vivo or in vitro, has not been disclosed. Nevertheless, it may be possible to culture certain types of cell types using the webs of the aforementioned patent.

According to one currently preferred embodiment of the present invention a fibrin sponge produced from a fibrinogen solution, wherein the fibrinogen solution is subjected to dialysis with a solution not requiring a complexing agent, serves as a scaffold for the growth of cells in vitro and in vivo. In another aspect the fibrin sponge is formed by the action of a thrombin solution on the dialyzed fibrinogen solution and subsequently subjected to freeze drying. Preferably, the fibrin sponge is seeded with desired cells, the cells allowed to proliferate and the sponge comprising the cells implanted at a site in need of tissue repair or regeneration. More preferably the cells are seeded on the sponge in combination with bioactive agents beneficial for the proliferation of said cells.

In the reconstruction of structural tissues like cartilage and bone, tissue shape is integral to function, requiring the molding of the matrix into three dimensional configuration articles of varying thickness and shape. Accordingly, the plasma matrix formed can be produced to assume a specific shape including a sphere, cube, rod, tube or a sheet. The shape is determined by the shape of a mold or support which may be made of any inert material and may be in contact with the matrix on all sides, as for a sphere or cube, or on a limited number of sides as for a sheet. The matrix may be shaped in the form of body organs or parts and constitute prostheses. Removing portions of the matrix with scissors, a scalpel, a laser beam or any other cutting instrument can create any refinements required in the three-dimensional structure.

The polymer matrix must be configured to provide both adequate sites for attachment and adequate diffusion of nutrients from the cell culture to maintain cell viability and growth until the matrix is implanted and vascularization has occurred. Cellular invasion is required by cells which can lay down the tissue to replace the implant and thus repair any defect which the implant is intended to repair. Failure to invade the structure of the implant in an efficient manner prevents vascularization which is required for new tissue to be able to sustain its life.

The plasma protein matrix according to further embodiments of the invention can be used as a matrix for growing cells or tissue culture in vitro. As will be shown in the examples below, the matrix of the invention is a plasma protein sponge. In its wet form, before drying, the matrix is a clot. In a dried form the matrix is a sponge. The matrices of the invention provide a relatively large surface area for cells to grow on and a mechanically improved scaffold for implantation.

Thus, the matrices of the invention are useful as products for in vitro and in vivo applications.

The plasma protein matrix, in its dry form, adheres exceptionally well to tissue surfaces. According to one embodiment of the present invention, a dry sponge of the invention is placed on the area where tissue regeneration is desired. A second sponge, onto which particular cells were cultured, is placed on top of the dry sponge. The wetted sponge of the invention adheres well to the dry sponge of the invention. During the healing process, the cells from the sponge onto which the cells were originally cultured migrate into the sponge adhering directly to the area of tissue regeneration. This system obviates the need for biological glue in instances where the wetted sponge does not adhere well.

According to certain embodiments of the invention, the plasma protein matrix is used as a support for chondrocyte growth and as a scaffold for neo cartilage formation. However, the plasma matrix of the invention may be used as a surface useful for tissue culture for any suitable cells, such as mesenchymal cells or other tissue forming cells at different levels of potency. For example, cells typically referred to as "stem cells" or "mesenchymal stem cells", are pluripotent, or lineage-uncommitted cells, which are potentially capable of an unlimited number of mitotic divisions to either renew a line or to produce progeny cells with the capacity to differentiate into any cell type can be grown on the matrix of the invention. In addition, lineage-committed "progenitor cells" can be grown on the matrix of the invention. A lineage-committed progenitor cell is generally considered to be incapable of an unlimited number of mitotic divisions and will eventually differentiate only into a specific cell type.

It will be appreciated that the matrix of the invention can support the growth and/or implantation of any type of cartilage or other suitable tissue. Furthermore, although the invention is directed predominantly to methods for growth and/or implantation of tissue in humans, the invention may also include methods for growth and/or implantation of tissues in any mammal.

The methods for seeding cells on the matrix are manifold. In a non-limiting example, the cells are adsorbed by placing the cells on the surface of the matrix or absorbed into the matrix by placing the sponge in a solution containing cells. Preferably the matrix is seeded with the desired cells by surface seeding, at a density of $10^4$ cells per $cm^3$, more preferably $10^5$ cells per $cm^3$.

Additives

The matrix of the invention, in certain embodiments may further include one or more antiseptics, such as methylene blue, and/or one or more drugs including antimicrobials such as antibiotics and antiviral agents; chemotherapeutic agents; anti-rejection agents; analgesics and analgesic combinations; anti-inflammatory agents and hormones such as steroids.

In other embodiments of the present invention the plasma protein matrix includes components which modulate the mechanical, physical and biological properties including elasticity, pore size, surface adhesion and ability to maintain cell growth and proliferation. These include materials belonging to the family of polysaccharides, anionic polysaccharides, glycosaminoglycans, or synthetic polymers, including hyaluronic acid, pectin, alginate, galactans, galactomannans, glucomannans, polyuronic acids, heparin, chondroitin sulfate, dextran sulfate, dermatan sulfate, heparan sulfate, keratan sulfate, hexuronyl hexosaminoglycan sulfate, inositol hexasulfate, sucrose octasulfate and PEG. Preferably the sponge is prepared with such auxiliary components such as dextran sulfate, PEG, glycerol and/or hyaluronic acid.

In addition, anti-fibrinogenic agents including tranexamic acid may be included in the matrix of the invention. These compounds prevent fibrinolysis and thus can be used for controlling the rate of degradation of fibrin in vivo. Tranexamic acid may be added to a final concentration ranging between 1% to 10%, preferably preferably 5%.

Bioactive agents, such as cytokines, growth factors and their activators etc., may be included in the matrix of the invention, or added to the cells to be seeded on the matrix for example, in order to enhance a therapeutic effect Incorporation of such agents into the sponge of the present invention provides a slow-release or sustained-release mechanism. For example, growth factors, structural proteins or cytokines which enhance the temporal sequence of wound repair, alter the rate of proliferation or increase the metabolic synthesis of extracellular matrix proteins are useful additives to the matrix of the present invention. Representative proteins include bone growth factors (BMPs, IGF) and fibroblast growth factors, including FGF2, FGF9 and FGF18 for bone and cartilage healing, cartilage growth factor genes (CGF, TGF-β) for cartilage healing, nerve growth factor genes (NGF) and certain FGFs for nerve healing, and general growth factors such as platelet-derived growth factor (PDGF), vascular endothelial growth factor (VEGF), insulin-like growth factor (IGF-1), keratinocyte growth factor (KGF), endothelial derived growth supplement (EDGF), epidermal growth factor (EGF) and other proteins which may enhance the action of the growth factors including heparin sulfate proteoglycans (HSPGs) their mimetics such as dextran sulfate, sucrose octa sulfate or heparin, and fragments thereof. Other factors shown to act on cells forming bone, cartilage or other connective tissue include retinoids, growth hormone (GH), and transferrin. Proteins specific for cartilage repair include cartilage growth factor (CGF), FGFs and TGF-β.

The proteins of the invention are polypeptides or derivatives or variants thereof, obtained from natural, synthetic or recombinant sources, which exhibit the ability to stimulate DNA synthesis and cell division in vitro of a variety of cells, including primary fibroblasts, chondrocytes, vascular and corneal endothelial cells, osteoblasts, myoblasts, smooth muscle and neuronal cells.

Additionally, cells genetically engineered to express the aforementioned proteins are including in the present invention. Preferred examples for cartilage repair uses periosteal cells, mesenchymal stem cells or chondrocytes per se or tansfected with cartilage growth factor genes selected from a group including transforming growth factory-β (TGF-β), certain FGFs or CGF; bone repair uses periosteal or other mesenchymal stem cells or osteocytes/osteoblasts per se or transfected with bone growth factor genes selected from a group including bone morphogenetic protein (BMP) family genes or fibroblast growth factor family genes; for nerve repair uses neural cells and neural support cells per se or transfected with genes selected from a group including nerve growth factor (NGF) gene or specific FGFs.

Furthermore, specific enzymes maybe admixed with the sponge of the invention in order to promote degredation of the proteoglycans and/or proteins present in the cartilage. Without wishing to be bound by theory, chondrocytes of the cartilage are embedded in the thick extracellular matrix (ECM) of the joint. Enzymes known in the art including collagenase, hyaluronidase, trysin, chymotrypsin, chondroitinase of the various types, degrade the ECM of the surface of the joint, thereby releasing chondrocytes that are able to invade the sponge of the invention to promote cartilage regeneration The plasma matrix of the invention is demonstrated as a fibrin sponge support for growing various cell types for implantation at a site of diseased or traumatized tissue. However, the matrix is a sponge comprising other plasma proteins and may be used per se, as an implanted scaffold on to which proximal cells in vivo may perfuse and grow; or as a scaffold for cell growth that is used for transplantation of cells to an injured tissue, or to any other suitable site in vivo. Thus, a person skilled in the art can adjust the procedures exemplified below in accordance with specific tissue requirements.

The following examples are intended to be merely illustrative in nature and to be construed in a non-limitative fashion.

EXAMPLES

Example 1

Isolation of Plasma Proteins from Whole Plasma

Fresh frozen plasma was received from the blood bank (Tel-Hashomer, Israel). The plasma (220 ml) was thawed in a 4° C. incubator over night, followed by centrifugation at 4° C. at approximately 1900 g for 30 min. The pellet was resuspended in 2.5 ml PBS with gentle rolling until a homogenized solution was seen. Tranexamic acid (anti-fibrinolytic; final 10%) and arginine (final 2%) were optionally added to the plasma protein fraction.

The total protein concentration was approximately 42–50 mg/ml as estimated by Bradford assay and SDS-PAGE (comparing to a standard).

Although detailed methods are given for the preparation of the plasma protein, it is to be understood that other methods of preparing plasma proteins are known in the art and are useful in the preparation of the matrix of the present invention. An example of a protocol for the preparation of a fibrinogen-enriched solution is given by Sims, et al. (Plastic & Recon. Surg. 101:1580–85, 1998).

Example 2

Extraction of Plasma Protein Fractions from Allogeneic or Autologous Blood

Materials:
1) Sodium citrate, 3.8% or any other pharmaceutically acceptable anti-coagulant
2) Ammonium sulfate $(NH_4)_2SO_4$, saturated (500 g/l)
3) Ammonium sulfate $(NH_4)_2SO_4$, 25%
4) Phosphate-EDTA buffer: 50 mM phosphate, 10 mM EDTA, pH 6.6
5) Tris-NaCl buffer: 50 mM Tris, 150 mM NaCl, pH 7.4
6) Ethanol, absolute 4° C.
7) Whole blood (Israel Blood Bank, Tel Hashomer Hospital or from patient)

Methods:
One bag of blood from the blood bank contained 450 ml and contained sodium citrate. To the 450 ml autologous blood, 50 ml of a 3.8% sodium citrate solution was added and the solution w as mixed gently.

The blood-sodium citrate was distributed to 50 ml tubes (40 ml/tube) and centrifuged at 2,100 g for 20 min. The supernatant plasma was collected into 50 ml tubes and re-centrifuged at 5000 g for 15 min. at 4° C. The supernatant plasma was collected into a flask, put on ice, and saturated ammonium sulfate solution was added at a ratio of one volume ammonium sulfate to 3 volumes of supernatant (1:3 volume ratio). A typical amount was 75 ml ammonium sulfate to 225 ml plasma. The solution was kept at 4° C. for 1.5 hrs with occasional mild shaking (magnetic stirring is not allowed).

The supernatant plasma was divided into 50 ml tubes (40 ml/tube) and centrifuged at 5000 g for 15 min at 4° C. The supernatant was discarded and each pellet washed with 10 ml 25% ammonium sulfate solution (pellet not dissolved).

Each pellet was dissolved in 6–7 ml of the phosphate-EDTA buffer. A sample, typically 100 μl of the solution, was kept for SDS-PAGE and clotting analyses.

The dissolved pellets were pooled and the ammonium sulfate precipitation was repeated by adding saturated ammonium sulfate to the plasma sample to achieve a 1:3 volume ratio (Typically, 25 ml ammonium sulfate to 75 ml plasma). The solution was kept at 4° C. for 1.5 hrs with occasional mild shaking, divided into 50 ml tubes and centrifuged at 5000 g for 15 min.

The supernatant was discarded and the pellets were dissolved in a volume of Tris-NaCl buffer that was equal to or less than the volume of phosphate-EDTA buffer used above. A typical total amount was about 45 ml.

The sample was dialyzed (SnakeSkin™ dialysis tubes, 3.5 kD cutoff, Pierce) for 3–4 hours or overnight at 4° C. in 1.5 liters of Tris-NaCl buffer. The dialyzed sample was centrifuged in high-speed resistant tubes at 21,000 g for 15 min at 4° C. to remove any insoluble material. The supernatant was collected and kept on ice.

The supernatant plasma was divided into 50 ml tubes. Chilled (EtOH) was added to a final concentration of 7%. (for example: 3.7 ml EtOH to 49 ml supernatant) and kept on ice for 30 min. It is essential that the solutions be chilled for the precipitate to form.

The solution was centrifuged at 5000 g for 15 min, the supernatant discarded and the pellet dissolved in the same volume (typically amount 45 ml) Tris-NaCl buffer. The solution was dialyzed overnight at 4° C. in 1.5 liter of Tris-NaCl Buffer. The dialyzed solution was centrifuged at 21,000, at 4° C. for 15 min, to eliminate any non-dissolved material.

Protein concentrations were determined using the Bradford method (Bradford (1976) Anal. Biochem. 72:248–254). The protein yields ranged from 0.2 to 0.6 mg per ml of full blood, with typical results of 0.4 to 0.5 mg/ml.

Clot formation ability was determined by adding 30 μl thrombin (100 U/ml; Omrix) to 70 μl plasma product (10 mg/ml), clotting should occur within 30 sec. Protein purity was determined by electrophoretic analysis of 50 μg of the sample on a 5% SDS-polyacrylamide gel and staining using Coommassie blue.

The remainder of the supernatant was collected, frozen and lyophilized until dry, 48 hours.

Example 3

Plasma Protein Matrix Preparation Method

Materials:
Tranexamic acid (5% final)
Calcium Chloride 5 mM
Thrombin (1000 units/ml, Omrix)

Methods 1:

The method for the preparation of the plasma protein matrix was optimized for protein and thrombin concentration as shown in Table 1 below. Samples prefixed with "1" tested optimisation of concentration of clottable protein. Samples prefixed "2" were tested for optimisation of concentration of thrombin in sponge. All experiments were carried out in triplicate.

TABLE 1

| Sample # | Plasma Protein Concentration | Thrombin Conc./mg protein |
| --- | --- | --- |
| 1–5 | 5 mg/ml | 1.5 IU |
| 1–10 | 10 mg/ml | 1.5 IU |
| 1–20 | 20 mg/ml | 1.5 IU |
| 1–30 | 30 mg/ml | 1.5 IU |
| 2–0.5 | 20 mg/ml | 0.5 IU |
| 2–4.5 | 20 mg/ml | 4.5 IU |

Results-1:

Sponges were analyzed by comparison of dry and wet physical properties.

The sponge made with 5 mg/ml protein (sample 1–5) shrank significantly upon freeze-drying. The sponges made with 10 or 20 mg/ml protein kept their structure after 24 hours in tissue culture medium, whereas the others were slightly deformed. This does not interfere with their use.

The concentration of thrombin determines the reaction time for the polymerization of the fibrin monomers. The concentration of 0.5 U thrombin/mg plasma proteins yielded a sponge with good physical and biological properties. The concentration of 1.5 U thrombin/mg plasma proteins was chosen because it gave a fast reaction but allowed the two solutions enough time to mix thoroughly before the reaction completes, but other concentrations are acceptable for obtaining a matrix with substantially similar properties.

Methods-2:

Sponges were made by mixing a plasma protein solution with a thrombin solution, casting, freezing and lyophilizing. Human plasma proteins, from different sources: allogeneic or autologous, with various levels of plasma proteins, were used having a protein concentration between 20–50 mg/ml. Commercial fibrinogen (Omrix) was tested, as well, at a concentration of 20 mg/ml.

Thrombin (1000 U/ml) was diluted 1:10 in a 5 mM calcium chloride solution. The final sponge formulation included tranexamic acid at a concentration of 5% or 10% depending on the plasma protein source.

The above two solutions (plasma protein and thrombin) were mixed together in a ratio of 21:9 respectively (for example 210 μl plasma protein and 90 μl thrombin solution), in the following order: A 48 well ELISA plate was coated with 90 μl of thrombin solution, and the plasma protein solution was added. The mixture was incubated at room temperature (~25° C.) for 10 minutes or until the clot formed, followed by freezing at −70° C. overnight (~16 h), and lyophilization under sterile conditions, −85° C. until dry for at least 16 hours and up to 24 h. Note that the final concentration of thrombin was 1.5 U/mg plasma proteins. The amount of thrombin may be varied depending on the desired polymerization rate of the matrix.

Results-2:

Sponges having substantially similar biomechanical features and biocompatibility were obtained from plasma protein solutions isolated from the different sources, allogeneic or autologous blood, whole plasma or commercial fibrinogen. These features include pore size, surface adherence, ability to maintain cell growth and proliferation and biocompatibility. This results shows that for the preparation of a plasma protein sponge of the present invention, a range of methods for preparing the plasma protein and a range of protein concentrations may be utilized.

Example 4

Scaffold Morphology and Mechanical Properties

Matrices for tissue engineering in general are characterized according to several criteria, including chemical nature, porosity, adhesion, biocompatibility and elasticity, amongst others (Hunziker, Osteoart. Cart., 10:432–465, 2002). Table II of the aforementioned reference lists several of the properties and the biological basis of these properties.

In the lab of the inventors, several of the properties have been measured. Porosity, important for cell migration was investigated by geometrical measurements using the light microscope by sectioning the scaffold into thick specimens. Specimens were mounted on slides and were stained by hematoxylin/eosin. An optical micrometer measured the pore size and the distance between neighboring pores.

FIG. 1A shows the plasma protein clot (10 mg plasma protein/ml) before drying. The pore size is in the $\mu$m (micron) size range. In the plasma protein sponge (FIG. 1B) (10 mg plasma protein/ml, after drying) the pores are in the 100 $\mu$m size range. The difference between the pore size of a plasma protein sponge of 20 mg protein/ml (FIG. 1D) and a plasma protein sponge of 10 mg fibrinogen/ml (FIG. 1B) is not notable and no difference was found in the cellular growth on the two scaffolds. It can be seen that the plasma protein sponges of the invention have a network of substantially regular pores compared with a collagen gel (FIG. 1C).

In its final form prior to use with cells the sponge is substantially dry and contains less than 10% residual moisture, more preferably less than 5% residual moisture and most preferably less than 3% residual moisture. This feature is measured by methods known in the art.

Mechanical property measurements were performed using a Chatillon TCD200 machine with a digital force gauge DF12. The distance between the clamps was set to 1.2 cm, and pull speed was set to 12.7 mm/min. Each plasma protein sponge was 2.5 cm long, 0.5 cm wide; and was fully lyophilized.

Deformation represents the elasticity of the sponge, i.e. the amount of pull as measured in millimeters (min) that may be exerted until the sponge tears. Force is calculated in kPa and represents the amount of energy required to tear the sponge strips. The thickness is incorporated in to the calculation.

Figure 2A:
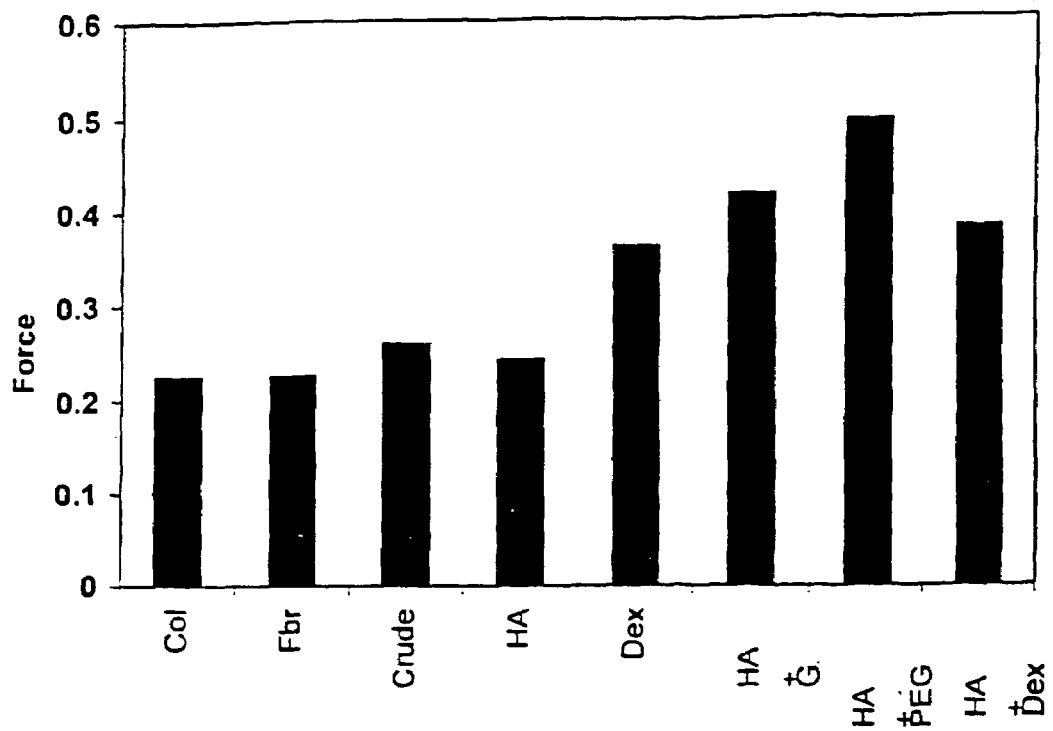
FIG. 2A and 2B represent mechanical properties of the sponges.
Figure 2B:
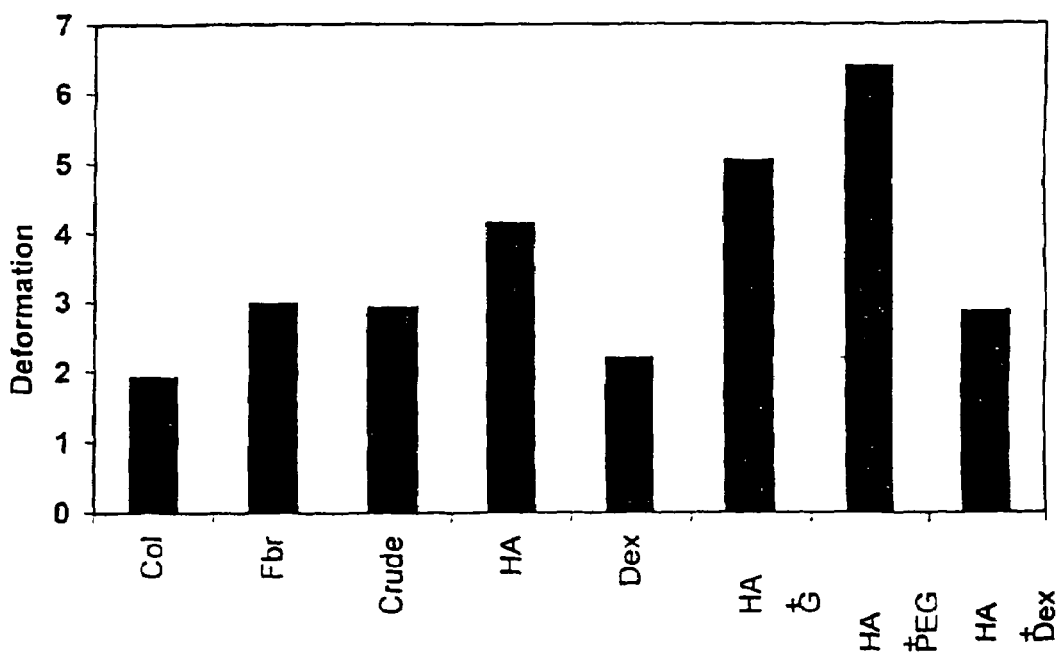

FIG. 2A represents the tensile strength measured in kPa in sponges comprising the different auxiliary components. FIG. 2B represents deformation of the same type of sponges. Shown is the average value of testing three sponges. The collagen (Col) sponge is commercially available (Ortec); the crude plasma sponge (crude) was prepared from crude plasma according to the protocol in example 1 (10 mg/ml fibrinogen). All sponges shown herein containing auxiliary components were prepared from commercially available fibrinogen (approximately 20 fibrinogen mg/ml). HA=hyaluronic acid (0.0024% final concentration), Dex=dextran sulfate (MW~10,000, 1% final concentration); PEG=PEG 300 (1.5% final concentration); G=glycerol (0.25% final concentration).

The sponges prepared from purified fibrinogen (Fbr) and those prepared from crude plasma proteins (crude) exhibit substantially identical mechanical properties. The sponges comprising both HA and PEG exhibit greatest tensile strength and elasticity. The sponges comprising dextran sulfate alone shows an increase in tensile strength, with no increase in elasticity. Each auxiliary agent appears to impart certain properties to the sponge. Microscopic analysis is performed to determine the pore size and pore uniformity of the sponges comprising the different components. Procedure for preparing sponges with additives is presented herein below.

Example 5

Procedure for Preparing Sponges Comprising Auxiliary Components

In a preferred embodiment of the present invention the matrix of the present invention may be prepared with certain additives, or auxiliary components. Additives including dextran sulfate, glycerol and hyaluronate (hyaluronic acid) were added to the sponges to alter certain mechanical and biological properties.

Mechanical and physical parameters were shown to be controlled by incorporating auxiliary components or additives. The additives may be removed after the matrix is formed in order to improve the biological properties of the matrix. All additives were filtered (0.2 $\mu$m) and were added to the plasma protein solution.

A list of the additives and concentrations tested are shown in the Table 2 below:

TABLE 2

| Additive | Concentration (% Final) |
| --- | --- |
| Glycerol | 0.005; 0.01; 0.05; 0.1; 0.25; 0.5; 1 |
| PEG* | 0.005; 0.05; 0.5; 1; 1.5 |
| Hyaluronic acid | 0.00024; 0.0024; 0.012; 0.024 |
| Dextran sulfate | 0.1; 1; 5; 10 |
| Glycerol + | 1 |
| Hyaluronic acid | 0.0024 |
| Glycerol + | 0.5 |
| Hyaluronic acid | 0.0024 |
| Glycerol + | 0.25 |
| Hyaluronic acid | 0.0024 |
| PEG + | 1.5 |
| Hyaluronic acid | 0.0024 |
| PEG + | 1.5 |
| Hyaluronic acid + | 0.0024 |
| Glycerol | 0.25 |
| Dextran sulfate + | 1 |
| Hyaluronic acid | 0.0024 |

*PEG = polyethylene glycol 300

Optimization experiments were carried out to determine the optimal concentration of the additives in terms of matrix flexibility, elasticity, pore size and cell growth capacity. The concentrations of the auxiliary components yielding good physical properties in terms of pore size, tensile strength and elasticity were 0.25% glycerol, 1.5% PEG, 0.0024% hyaluronic acid or 1% dextran sulfate. One preferred combination of two or more components is listed in table 2.

The additives impart beneficial properties, including surface, mechanical and/or biological properties, to the sponge during its preparation. A currently most preferred embodiment in accordance with the present invention is a sponge comprising dextran sulfate.

Certain additives may be detrimental to cell growth and may therefore be removed following the freeze drying step. The sponge is rehydrated by washing in sterile, distilled water or PBS and is used per se or may be relyophilized to remove all moisture. A currently preferred embodiment provides a sponge prepared containing one or more additives as described above, wherein the sponge is washed following the freezing-lyophilization step and the sponge relyophilized to remove all residual moisture.

Example 6

Dissolution Rate

The rate of sponge dissolution measures the level of crosslinking that the plasma protein have undergone.

Two experiments were carried out: 1-Freshly made versus one month old sponges stored at room temperature and 2: two month old sponges stored under different conditions.

1. Freshly made and one month aged sponges were placed into 0.75 ml 10M Urea, and gently shaken. A sample of urea was taken every 5, 15, 20, 30, 40 minutes. The amount of protein in the urea, i.e. dissolution rate of fibrin sponges was determined by the Bradford method.

Figure 3A:
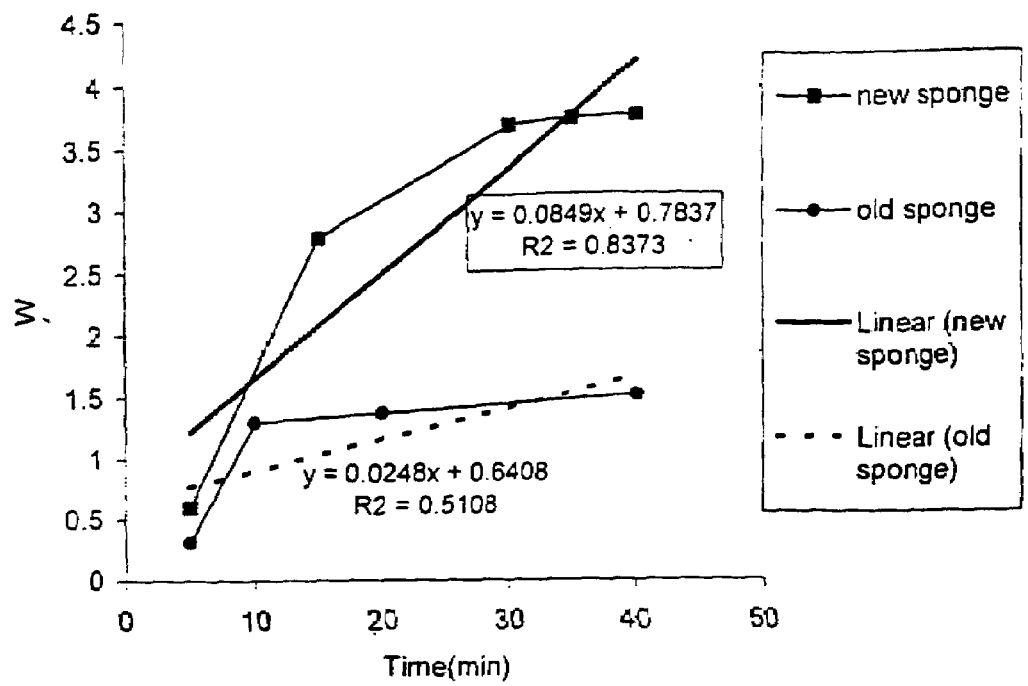
FIG. 3A and 3B shows the dissolution rate of fibrin sponges in urea.

FIG. 3A shows that a freshly made sponge dissolved in urea at a rate of 0.085 mg/min while the older sponges dissolved at a rate of 0.025 mg/min. This suggests that the aged sponge is more cross-linked than the fresh sponge.

2. Sponges were stored for two months under two different conditions:
   a. Inert atmosphere $N_2$ (g)
   b. Open air (standard atmosphere).

Following two months, the sponges were tested as above.

Figure 3B:
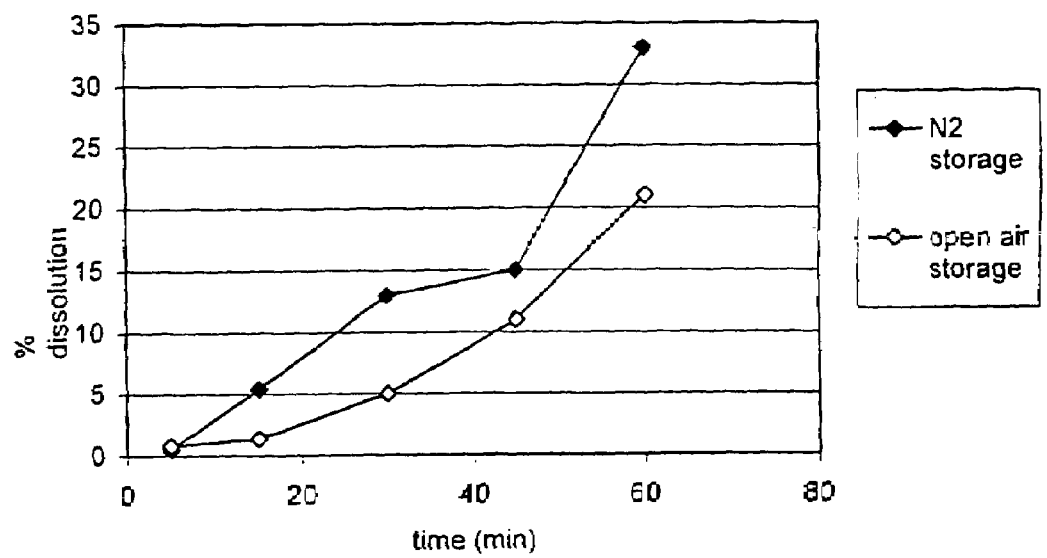

FIG. 3B shows that the sponges exposed to air undergo cross-linking at faster rates than those stored under inert conditions.

Example 7

Cell Seeding

Different methods of seeding cells onto the sponge may be used. Important to seeding is cell adherence, migratory capacity and proliferation of cells within the matrix. Cells may be suspended in medium, PBS, or any biocompatible buffer alone or in the presence of bioactive agents. Cells may be seeded by placing a drop of liquid containing cells on the sponge and allowing the cells to adsorb into the sponge. Alternatively, the cells in the liquid may be absorbed into the sponge by placing the sponge in a container holding a suspension of cells.

Materials and Methods:

Cultured cells are prepared in growth medium (MEM), and placed on top of a sponge at a density of between $10^2$–$10^6$ cells per standard 300 µl plasma protein sponge (approximately 0.2 cm$^3$) in a microtiter plate having 48 wells. Different volumes of growth media are added and the cells allowed to grow for various time periods. It is to be understood that the sponge of may be of varying sizes, shapes and thickness.

Following three-days, 1 week and three week incubation for the seeded sponges, the sponges are sectioned and the cell invasion and proliferation observed. Cell proliferation is determined as described in Example 9.

Example 8

Cell Isolation and Culturing

Reagents:

Collagenase Type 2; Worthington Biochemical Corp. (Cat. #: 4147)

Stock solution: 1700 units/ml in medium (in MEM)

Minimal Essential Medium (MEM) Gibco BRL (cat: 21090-022)

Fetal Bovine Serum (FBS); Gibco BRL (cat 16000-044)

L-Glutamine Solution; Gibco BRL (cat: 25030-024)

Complete medium: Minimal Essential Medium (MEM) supplemented with 10% fetal calf serum (FCS), 2 mM L-Glutamine and 100 U/ml penicillin, and 100 µg/ml streptomycin Preparation of Implants for Articular Cartilage The sponge of the present invention may be used as a cell bearing scaffold for tissue repair and regeneration In one aspect, the cells are cultured on the sponge in vitro prior to implantation. In a preferred aspect, the sponge is seeded with cells immediately before implantation and the cells allowed to grow and proliferate in vivo.

Cartilage biopsies from fresh pig cartilage were sectioned into small pieces, approximately of 3–4 mm thick, washed aseptically with PBS and placed in a new tube containing 3 ml MEM medium. The cartilage may be obtained from any vertebrate species, and is preferably allogeneic or autologous.

Collagenase type II was diluted 1:5 and 1 ml was added to the cartilage pieces and the mixture was shaken gently in a 37° C. incubator over night. When most of the sample was digested, the suspension was poured through sterile gauze to remove matrix debris and undigested material. The filtrate was centrifuged and washed twice to remove residual enzyme.

The number of cells was determined by a hemocytometer and viability was determined by trypan blue exclusion. The cells were plated in 150 cm$^2$ tissue culture flasks in 30 ml of culture medium at a concentration of 5×10$^6$ cells/ml. Flasks were placed in a 37° C. incubator at 5% $CO_2$ atmosphere and 95% humidity. The culture medium was changed every three to four days. The cells adhere and become confluent following one week incubation.

At confluence, the cell medium was removed and 3 ml trypsin-EDTA solution were added. Thirty ml MEM+FBS was added, the solution was centrifuged at 800 g for 10 minutes. The supernatant was removed, the pellet dispersed and the cells were counted. To create a cell-bearing matrix, $10^2$–$10^6$ cells were seeded on a plasma protein scaffold of 9 mm in diameter and a thickness of 2 mm (approximately 0.2 cm$^3$). The matrices were placed in a 37° C. incubator for 1 hour and 1 ml of fresh medium was added to each. The medium was replaced with fresh medium and every few days the matrices were taken to cell proliferation and differentiation analysis.

Results:

FIGS. 4A–D show that the plasma matrix is able to support calf chondrocyte proliferation. A 3 to 5 fold increase in cell number was observed from an initial state (FIG. 4A) up to cell confluence (FIGS. 4B through 4D). A histological section of a one month collagen implant for hematoxylin and eosin showed that the cells on the surface of the collagen sponge are smaller and retain their spherical shape (see FIGS. 4C and 4D). In the interior part of the collagen sponge cells re-organized in tissue which resembles fibro-cartilage, whereas in the plasma protein sponge (FIG. 4A-D) cells are well distributed and spaced apart from each other, embedded in a thick hyaline like extracellular matrix and retain their round cell morphology typical of mature articular chondrocytes. Small islets of retained fibrin demonstrate the capacity of the cells to completely brake down the matrix and replace it with cartilagenous matrix. These results suggest that the success of tissue-like formation, in vitro, strongly depends on the specific cell-matrix material. The fibrin sponge according to an embodiment of the invention is shown to be a superior matrix for cartilage tissue formation than the collagen sponge.

Figure 5:
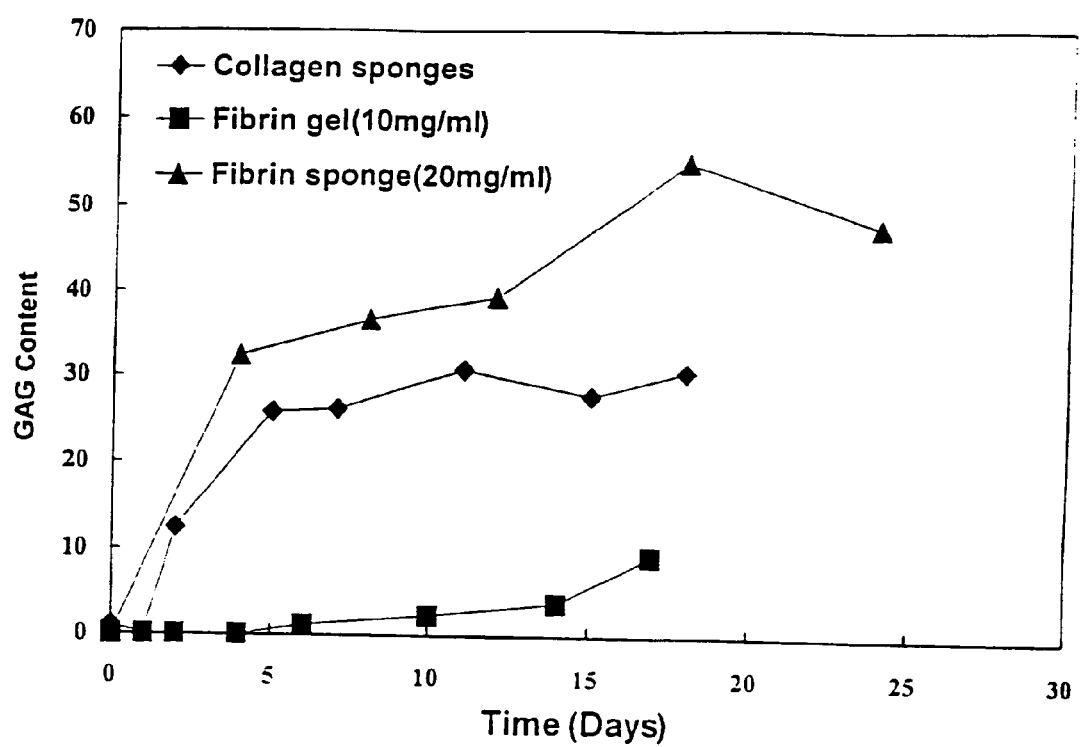
FIG. 5 is a graph showing the glycosaminoglycan (GAG) content of cells grown on a plasma protein sponge according to an embodiment of the invention compared with cells grown on a fibrin clot and on a commercially available collagen sponge.

Further, part of the cell population grown on the above matrices expressed several of the chondrocyte differentiation markers. One of several phenotypes expressed during chondrocyte differentiation is glycosaminoglycan (GAG) production. The production of GAGs was identified in histological staining using Acian blue and quatitated using the DMB (3,3'-dimethoxybenzidine dihydrochloride) Dye method. FIG. 5 shows the results of the GAG content in calf chondrocytes grown on three different matrices; collagen sponges, fibrin clot (10 mg/ml) and plasma protein sponges (20 mg/ml). It is apparent from the graphs presented in FIG. 5 that cells grown on the plasma protein sponge and/or fibrin clot show a significantly higher GAG content than cells grown on the collagen sponge matrix. This experiment demonstrates the ability of cells to undergo differentiation on the plasma protein sponge.

Example 9

Cell Proliferation Assay

Proliferation of the cartilage cells on the matrix of the invention was quatitated by one of two methods, CyQUANT® (Molecular Probes) or XTT reagent (Biological Industries, Co.). The plasma protein matrix was dissolved in collagenase or other enzymes and the cells collected by centrifugation and subjected to analysis according to manufacturer's protocols.

Figure 6:
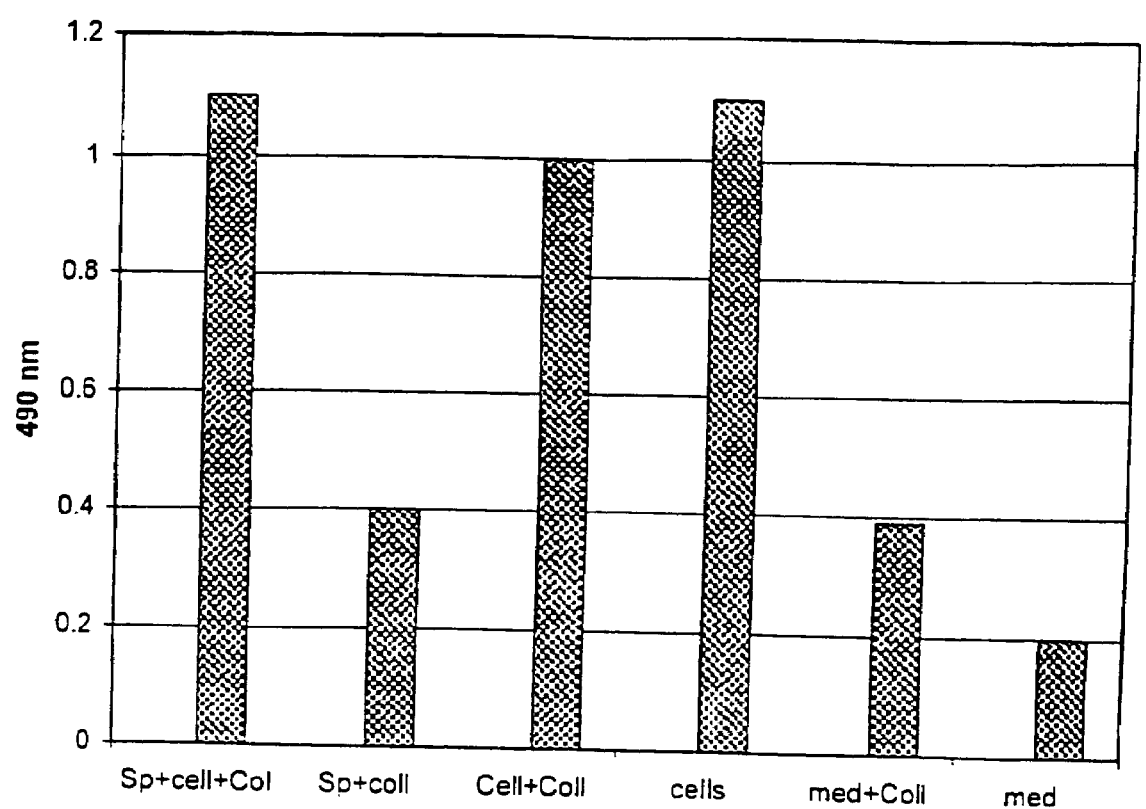
FIG. 6 shows the proliferation of articular chondrocytes in the presence of the plasma protein sponge and collagenase.

In one experiment, human articular chondrocytes ($10^6$ cells/100 ul) were grown in the presence of the matrix of the invention and collagenase in microwell plates. The cells were grown overnight in MEM, 34 U collagenase was added and the cells or cells+sponge incubated for four hours. XTT reagent was added for 3–4 hours and the plates were read in an ELISA reader at A490 mm. Results are shown in FIG. 6. As can be seen the proliferation rate of the cell was not impaired by the presence of the sponge nor by the addition of the collagenase.

Example 10

Goat Articular Cartilage Repair Model

A comparative study to evaluate the use of implanted sponges in knee injuries in goats was performed.

The goals of the study were to compare freshly prepared sponges to aged spones and a commercial collagen matrix in terms of inflammatory, response, ability to adhere to the injured surface, to test the capacity of the sponges to induce the growth of hyaline cartilage.

Materials and Methods:

6 goats were selected for the trial and were randomly assigned to one of the treatment groups.

The different sponges (matrices) tested include:

1: freshly prepared plasma protein sponges

2: sponge incubated at 60° C. (incubated at 60° C. for 24 hours following casting)

3: aged sponges (4–6 months old, room temperature storage).

4: collagen (Ortec).

Antibiotics:

2 ml of amoxycillin was injected IM immediately before the procedure and once a day for 4 days after the procedure.

Anesthesia:

Pre-medication: 0.2 ml xylazine 2% per 25 kg body weight was administered IM.

Induction: Once the goats were dazed an I.V. venflon was inserted.

Formulation of 1 ml valium (1 mg)+2 ml Ketamine (100 mg/ml) 1 ml/25 kg BW bolus was administered through the venflon. An additional 0.5 ml can be added as needed. For procedures longer than 30 minutes, intubations and gas (HALTOGEN™, or isofloran) anesthesia was administered.

Procedures for Performing the Wound:

Animals were shaved in both knees and were washed with disinfectant.

Knees were exposed on the lateral side and the patella was dislocated laterally and the cartilage exposed.

Four partial thickness defects (6 mm) were created in the joint surface of the femoral condyles of the knee using a scalpel without penetrating the sub-chondral bone. The defect area was washed using saline.

Procedure for Transplanting the Sponge:

The lyophilized matrices were implanted and adhered to the defect. Optionally a fibrin-based biological glue may be used. The patella was relocated and the sinovia and skin closed using Vicryll sutures. The skin was cleaned with an iodine ointment.

Analgesia: 0.05 mg/kg buprenorphine was injected SC (subcutaneous) just before the procedure and at the end of the same day Follow Up and Histological Evaluation:

At the end of the follow up period (6 or 10 weeks) goats were sacrificed and tissue taken for histological evaluation: Knee's were evaluated for mobility, and appearance. Histological sections were prepared from the injured area and from 2–3 mm margins. The tissue was de-calcified and slides prepared in a standard procedure.

Slides were stained with hematoxylin-eosin and alcianblue staining. Immunohistological analyses are performed, including immunohistochemistry using antibodies to cell type markers or in situ RNA hybridization using RNA or DNA probes.

Histological evaluation was performed to measure the following parameters: Characteristics of the neo-formed tissue, regularity of the joint surface of the regenerated tissue, structural integrity of the regenerated tissue, endochondral ossification and state of the cells in the remaining cartilage.

Results:

Table 3 presents a description of the experiment and the results of the histology analysis.

TABLE 3

| Goat | Treatment | Time | Results |
| --- | --- | --- | --- |
| 2 | Fresh sponges | 6 weeks | Minimal inflammation, minimal fibrous tissue |
| 943 | 60° C. sponges | 6 weeks | Inflammation as seen by presence of histiocytes; fibrous tissue |
| 143 | Aged sponges | 6 weeks | Minimal inflammation, minimal fibrous tissue. Mesenchymal cell |

TABLE 3-continued

| Goat | Treatment | Time | Results |
|---|---|---|---|
| | | | proliferation in and around wound. |
| 945 | Fresh sponges | 10 weeks | No inflammation; mesenchymal cell proliferation |
| 183 | Collagen sponges | 10 weeks | Massive inflammation |
| 930 | 60° C. sponges | 10 weeks | Minimal inflammation; Mesenchymal cell proliferation. |

Figure 7:
FIG. 7 shows the results of the plasma protein sponge implantation into goats.
Figure 7:
Figure 7:
Figure 7:
Figure 7:
Figure 7:

FIG. 7 shows the knee joints of the goats following the experiment.

Example 11

One-Step Procedure for Treating Damaged Cartilage: Suitable for Arthroscopy or Hemi-Arthrotomy Autologous chondrocyte implantation has proven clinically effective in restoring hyaline-like cartilage to isolated chondral defects of the knee. The present therapies include three major steps:
1. Diagnostic Arthroscopy and biopsy of healthy cartilage.
2. Cultivation of cells.
3. Injection of cultured chondrocytes into the lesion under a periosteal flap, which is taken from the tibia and sutured over the lesion.

A variation of this technique provides incorporation of cells into a biodegradable material, including the matrix of the present invention. A less traumatic method is presented herein, wherein the patient undergoes a single surgical procedure for cartilage repair.

Procedure

A patient with a cartilage defect is called to the physician's office for a consultation several days prior to the arthroscopy or hemi-arthrotomy. Blood (approximately 100–250 ml) is drawn and plasma proteins are isolated. A plasma protein matrix, or several matrices, is prepared, labeled and stored aseptically until the day of the surgery.

On the day of the surgery, a small piece of healthy cartilage the patient's joint is removed, cut into small pieces and placed in a test tube containing collagenase, hyaluronidase or other cartilage degrading enzymes, or combinations thereof.

In the meantime, the surgeon will treat the defective region of the joint by removing damaged tissue, cleansing and preparing the area for an implant The prepared matrix is removed from its container and cut to fit the defective domain. Following approximately 20–30 minutes of enzymatic treatment, the cells and small pieces of cartilage are spun down in a tabletop centrifuge, rinsed in PBS and resuspended in a small amount (50 ul–1000 ul) of PBS. The surgeon seeds the cells onto the sponge, in situ. Alternatively the cells are absorbed into the sponge and the cell-bearing sponge implanted into the defective joint region. Optionally, extracellular matrix degrading enzymes and or other bioactive agents including growth factors and/or anti-inflammatory compounds are added to the sponge. In certain instances the surgeon will place a dry sponge directly onto the injured area, optionally add enzyme solution to said sponge and place a second, cell-bearing sponge on top of the first sponge. The joint is closed and is treated as customary for an arthroscopic or hemi-arthrotomy procedure and the patient is released to recover.

Kit

A kit comprising the components useful for practicing the method of the invention, will allow for the convenient practice of the method of the invention in a surgical setting. In a preferred embodiment, a kit of the invention will provide sterile components suitable for easy use in the surgical environment including, sterile solutions (saline, enzymes) a sterile, cell-free matrix material suitable for supporting autologous chondrocytes that are to be implanted into an articular joint surface defect and instructions for use. Although the matrix may be of any material that is biocompatible, non-immunogenic and has the ability to maintain cell growth and proliferation, the matrix is preferably prepared from allogeneic plasma, more preferably from autologous plasma Example 12

Release of Bioactive Agents

One factor which may facilitate the development of tissues on the matrices is the delivery of growth factors or other biological agents into the local environment The incorporation and release of growth factors from these matrices is assessed in vitro or in vivo using radiolabeled or tagged growth factors, for example fluorescent-labeled, alkaline phosphatase labeled or horseradish peroxidase-labeled growth factor. The fraction and rate of released agent is measured by following the radioactivity, fluorescence, enzymatic activity or other attributes of the tag. Similarly, release of enzymes from the matrix is determined by analyzing enzymatic activity into the microenvironment in an in vitro or in vivo assay.

While the present invention has been particularly described, persons skilled in the art will appreciate that many variations and modifications can be made. Therefore, the invention is not to be construed as restricted to the particularly described embodiments, rather the scope, spirit and concept of the invention will be more readily understood by reference to the claims which follow.

What is claimed is:

1. An elastic freeze-dried biocompatible porous fibrin matrix useful as a scaffold for growing cells, wherein the matrix has substantially regular pores and a residual moisture below 3% and is obtained by mixing lplasma proteins comprising fibrinogen and Factor XIII with thrombin and at least one anti-fibrinolytic agent in substontial absence of organic chelating agents.

2. The matrix according to claim 1 wherein the plasma proteins are present with at least 0.5 units of thrombin per milligram of protein.

3. The matrix according to claim 1 wherein at least one of the plasma proteins is autologous to a patient in need of the matrix.

4. The matrix according to claim 1 wherein all the plasma proteins are autologous to a patient in need of the matrix.

5. The matrix according to claim 1 wherein the anti-fibrinolytic agent is tranexamic acid.

6. The matrix according to claim 1 further comprising at least one auxiliary component selected from the group consisting of polysaccharides, anionic polysaccharides, glycosaminoglycans, or synthetic polymers.

7. The matrix according to claim 6 wherein the auxiliary component is selected from a group consisting of hyaluronic acid, pectin, alginate, galactans, galactomannans, glucomannans, polyuronic acids, heparin, chondroitin sulfate, dextran sulfate, dermatan sulfate, heparan sulfate, keratan sulfate, hexuronyl hexosaminoglycan sulfate, inositol hexasulfate, sucrose octasulfate and polyethylene glycol.

8. The matrix according to claim 7 wherein the wherein the auxiliary component is dextran sulfate or hyaluronic acid.

9. The matrix according to claim 1 wherein the cells are stem cells or progenitor cells.

10. The matrix according to claim 1 wherein the cells are selected from the group consisting of chondrocytes, osteocytes, hepatocytes and mesenchymal, epithelial, urothelial, neuronal, pancreatic, renal and ocular cell types.

11. The matrix according to claim 1 wherein the cells attain a density of at least $10^4$ cells per $cm^3$.

12. The matrix according to claim 1 further comprising at least one bioactive agent, selected from the group consisting of growth factors, cytokines, enzymes, anti-microbials, and anti inflammatory agents.

13. The matrix according to claim 1 having pores in the size range of 50–300 microns.

14. The matrix of claim 1, wherein the plasma proteins are mixed with the thrombin in the presence of the calcium ions and the at least one anti-fibrinolytic agent under conditions suitable for clotting, optionally with adding of at least one auxiliary component thereto; and the mixture of plasma protiens, thrombin, anti-fibrinolytic agent and optional auxiliary agent are cast upon a solid support prior to clotting; the clotted mixture is frozen; and the clotted mixtire is lyophilized to obtain the matrix.

15. The matrix according to claim 14 wherein the plasma proteins comprise at least fibrinogen and factor XIII.

16. The matrix according to claim 14 wherein at least one of the plasma proteins is autologous.

17. The matrix according to claim 14 wherein all the plasma proteins are autologous.

18. The matrix according to claim 14 wherein the plasma proteins are mixed with at least 0.5 units of thrombin per mg protein.

19. The matrix according to claim 14 wherein the anti-fibrinolytic agent comprises tranexamic acid in an amount of at least 5%.

20. The matrix according to claim 14 wherein the at least one auxiliary component is present and is selected from the group consisting of polysaccharides, anionic polysaccharides, glycosaminoglycans, and synthetic polymers.

21. The matrix according to claim 14 wherein the at least one auxiliary component is present and is selected from the group consisting of hyaluronic acid, pectin, alginate, galactans, galactomannans, glucomannans, polyuronic acids, heparin, chondroitin sulfate, dextran sulfate, dermatan sulfate, heparan sulfate, keratan sulfate, hexuronyl hexosaminoglycan sulfate, inositol hexasulfate, sucrose octasulfate and polyethylene glycol.

22. The matrix according to claim 20 wherein the auxiliary component is present and is dextran sulfate or hyaluronic acid.

23. The matrix of claim 1, wherein the plasma proteins with thrombin in the presence of calcium ions and at least one anti-fibrinolytic agent under conditions suitable for clotting, optionally with adding of at least one auxiliary component; and the mixture of plasma proteins, thrombin, anti-fibrinolytic agent and optional auxiliary agent are cast upon a solid support prior to clotting; the clotted mixture is frozen; and the clotted mixture is lyophilized to obtain a sponge; and the sponge is cut into sections of desired shape; to obtain the matrix; and further the sections are seeded with cells; the cells are grown on the sections until the cells reach a density of at least 104 cells per $cm^3$; and the seeded sections are implanted in vivo.

24. The matrix according to claim 23 wherein the plasma proteins comprise at least fibrinogen and factor XIII.

25. The matrix according to claim 23 wherein at least one of the plasma proteins is autologous.

26. The matrix according to claim 23 wherein all the plasma proteins are autologous.

27. The matrix according to claim 23 wherein the plasma proteins are mixed with at least 0.5 units of thrombin per mg protein.

28. The matrix according to claim 23 wherein the anti-fibrinolytic agent comprises tranexamic acid in an amount of at least 5%.

29. The matrix according to claim 23 wherein the at least one auxiliary component is present and is selected from the group consisting of polysaccharides, anionic polysaccharides, glycosaminoglycans, and synthetic polymers.

30. The matrix according to claim 23 wherein the auxiliary component is present and is selected from the group consisting of hyaluronic acid, pectin, alginate, galactans, galactomannans, glucomannans, polyuronic acids, heparin, chondroitin sulfate, dextran sulfate, dermatan sulfate, heparan sulfate, keratan sulfate, hexuronyl hexosaminoglycan sulfate, inositol hexasulfate, sucrose octasulfate and polyethylene glycol.

31. The matrix according to claim 23 wherein the auxiliary component is present and is dextran sulfate or hyaluronic acid.

32. The matrix according to claim 23 wherein the at least one auxiliary component is present and is a bioactive agent selected from the group consisting of growth factors, cytokines, enzymes, anti microbials, and anti-inflammatory agents.

33. The matrix according to claim 23 wherein the cells are selected from the group consisting of chondrocytes, hepatocytes, and osteocytes, mesenchymal, epithelial, urothelial, neuronal, pancreatic, renal and ocular cell types.

34. The matrix of claim 1, wherein the plasma proteins are mixed with the thrombin in the presence of the calcium ions and at least one anti-fibrinolytic agent under conditions suitable for clotting, optionally with adding of at least one auxiliary component; and the mixture of plasma proteins, thrombin, anti-fibrinolytic agent and optional auxiliary agent are cast upon a solid support prior to clotting; the clotted mixture is frozen; and the clotted mixture is lyophilized to obtain a sponge having no more than 3% residual moisture; the sponge is optionally washed to remove soluble auxiliary components; optionally the washed sponge is re-lyophilized to reduce the residual moisture to no more than 3%; the sponge is cut into sections of desired shape to obtain the matrix; and the sections of matrix are implanted in situ.

35. The matrix according to claim 34 wherein the plasma proteins comprise at least fibrinogen and factor XIII.

36. The matrix according to claim 34 wherein at least one of the plasma proteins is autologous.

37. The matrix according to claim 34 wherein all the plasma proteins are autologous.

38. The matrix according to claim 34 wherein the plasma proteins are mixed with at least 0.5 units of thrombin per mg protein.

39. The matrix according to claim 34 wherein the antifibrinolytic agent comprises tranexamic acid in an amount of at least 5%.

40. The matrix according to claim 34 wherein the at least one auxiliary component is present and is selected from the group consisting of polysaccharides, anionic polysaccharides, glycosaminoglycans, or synthetic polymers.

41. The matrix according to claim 34 wherein the at least one auxiliary component is present and is selected from the group consisting of hyaluronic acid, pectin, alginate, galactans, galactomannans, glucomannans, polyuronic acids, heparin, chondroitin sulfate, dextran sulfate, dermatan sulfate, heparan sulfate, keratan sulfate, hexuronyl hexosaminoglycan sulfate, inositol hexasulfate, sucrose octasulfate and polyethylene glycol.

42. The matrix according to claim 34 wherein the at least one auxiliary component is present and is dextran sulfate or hyaluronic acid.

43. The matrix according to claim 34 wherein the at least one auxiliary component is present and is a bioactive agent selected from the group consisting of growth factors, cytokines, enzymes, anti microbials, and anti-inflammatory agents.

44. The matrix according to claim 34 wherein the cells are selected from the group consisting of chondrocytes, osteocytes, hepatocytes, and epithelial, urothelial, neuronal, mesenchymal, pancreatic, renal and ocular cell types.

45. The matrix according to claim 34 which further comprises seeding the sections with cells and growing the cells on the sections until the cells reach a density of at least $10^4$ cells per $cm^3$.

46. The matrix according to claim 34 which further comprises seeding the sections with cells in vivo at a site of treatment.

47. An implant comprising the matrix according to claim 14.

48. A method for treating injured tissue, the method comprising the step of implanting into an injury site an implant according to claim 47.

49. The method according to claim 48 wherein the injured tissue to be treated is skeletal tissue.

50. A porous coating comprising the matrix according to claim 1.

51. The coating according to claim 50 wherein the matrix further comprises at least one auxiliary component selected from the group consisting of polysaccharides, anionic polysaccharides, glycosaminoglycans, or synthetic polymers.

52. The matrix according to claim 1 wherein the plasma proteins and thrombin is mixed in the presence of calcium ions.

53. The matrix according to claim 1 wherein the matrix has a tensile strength of at least about 0.2 kPa.

* * * * *

UNITED STATES PATENT AND TRADEMARK OFFICE
CERTIFICATE OF CORRECTION

PATENT NO. : 7,009,039 B2  
DATED : March 7, 2006  
INVENTOR(S) : Yayon et al.

It is certified that error appears in the above-identified patent and that said Letters Patent is hereby corrected as shown below:

Title page,
Item [56], References Cited, OTHER PUBLICATIONS,
"Sims, C. Derek M.D. et al." reference, delete "Boston and Cambridge, Mass." and insert -- Plastic & Reconstructive Surgery --.
"A. Haisch et al." reference, after "Medical & Biological" delete "Engineerin" and insert -- Engineering --.

Column 24,
Line 49, delete "lplasma" and insert -- plasma --.
Line 51, delete "substontial" and insert -- substantial --.

Column 25,
Line 8, after "claim 7" delete "wherein the".
Line 62, before "with thrombin in the presence of" insert -- are mixed --.

Column 26,
Line 2, delete "shape;" and insert -- shape --.

Signed and Sealed this

Sixth Day of June, 2006

JON W. DUDAS  
*Director of the United States Patent and Trademark Office*